(12) United States Patent
Hagelin et al.

(10) Patent No.: US 9,167,802 B2
(45) Date of Patent: Oct. 27, 2015

(54) METHOD OF USING BIOLOGICALLY-RELEVANT CHEMICAL ATTRACTANTS FOR MARINE PREDATORS

(71) Applicants: Julie Claire Hagelin, Ester, AK (US); Janice Morrison Straley, Sitka, AK (US)

(72) Inventors: Julie Claire Hagelin, Ester, AK (US); Janice Morrison Straley, Sitka, AK (US)

(73) Assignee: Julie C. Hagelin, Ester, AK (US)

( * ) Notice: Subject to any disclaimer, the term of this patent is extended or adjusted under 35 U.S.C. 154(b) by 0 days.

(21) Appl. No.: 14/262,515

(22) Filed: Apr. 25, 2014

(65) Prior Publication Data

US 2014/0318476 A1    Oct. 30, 2014

Related U.S. Application Data

(60) Provisional application No. 61/816,656, filed on Apr. 26, 2013.

(51) Int. Cl.
| | | |
|---|---|---|
| *A01K 97/04* | (2006.01) |
| *A01K 85/00* | (2006.01) |
| *A01K 29/00* | (2006.01) |
| *A01N 25/04* | (2006.01) |
| *A01K 79/02* | (2006.01) |

(52) U.S. Cl.
CPC ............... *A01K 29/00* (2013.01); *A01K 79/02* (2013.01); *A01N 25/04* (2013.01)

(58) Field of Classification Search
CPC ....... A01N 25/00; A01N 25/04; A01N 25/06; A01N 31/00; A01N 31/04; A01N 59/02; A01N 59/04
USPC ..................... 426/1; 424/84; 43/42
See application file for complete search history.

(56) References Cited

U.S. PATENT DOCUMENTS

| | | | | | |
|---|---|---|---|---|---|
| 4,362,748 | A | * | 12/1982 | Cox | 426/1 |
| 4,801,448 | A | * | 1/1989 | Wilson et al. | 424/84 |
| 4,826,691 | A | * | 5/1989 | Prochnow | 426/1 |

OTHER PUBLICATIONS

Dell'Ariccia et al. "Olfactory foraging in temperature waters: sensitivity to dimethylsulfide of shearwaters in the Atlantic Ocean and Mediterranean Sea", http://Jeb.biologist.org/content/217/10/1701.full, first published online Feb. 13, 2014.*
Nevitt "The Neuroecology of Dimethy Sulfide: A Global-Climate Regulator turned Marine Infochemical", http://icb.oxfordjournals.org/content/early/2011/08/3/icb.icro093.full, published on line Aug. 31, 2011.*
Nevitt et al. "Dimethyl Sulphide as a Foraging Cue for Antarctic Procellariiform Seabirds", Nature vol. 376 Aug. 24, 1995.*
Kowalewsky et al. "High Olfactory Sensitivity for Dimethyl Sulphide in Harbour Seals", http://rsbl.royalsocietypublishing.org/, published online Sep. 1, 2005.*

* cited by examiner

*Primary Examiner* — Nina Bhat

(57) ABSTRACT

Described herein is a method of using biologically-relevant attractants for marine predators through deployment of the attractants into air and/or water in concentrations manners which will encourage the specific marine predators to move toward the deployment source. The method could be used in a number of situations, including, but not limited to, situations in which animals are in a hazardous situation, such as the immediate danger of an oil spill or clean-up activities in which the marine predators must be enticed to safety.

18 Claims, 2 Drawing Sheets

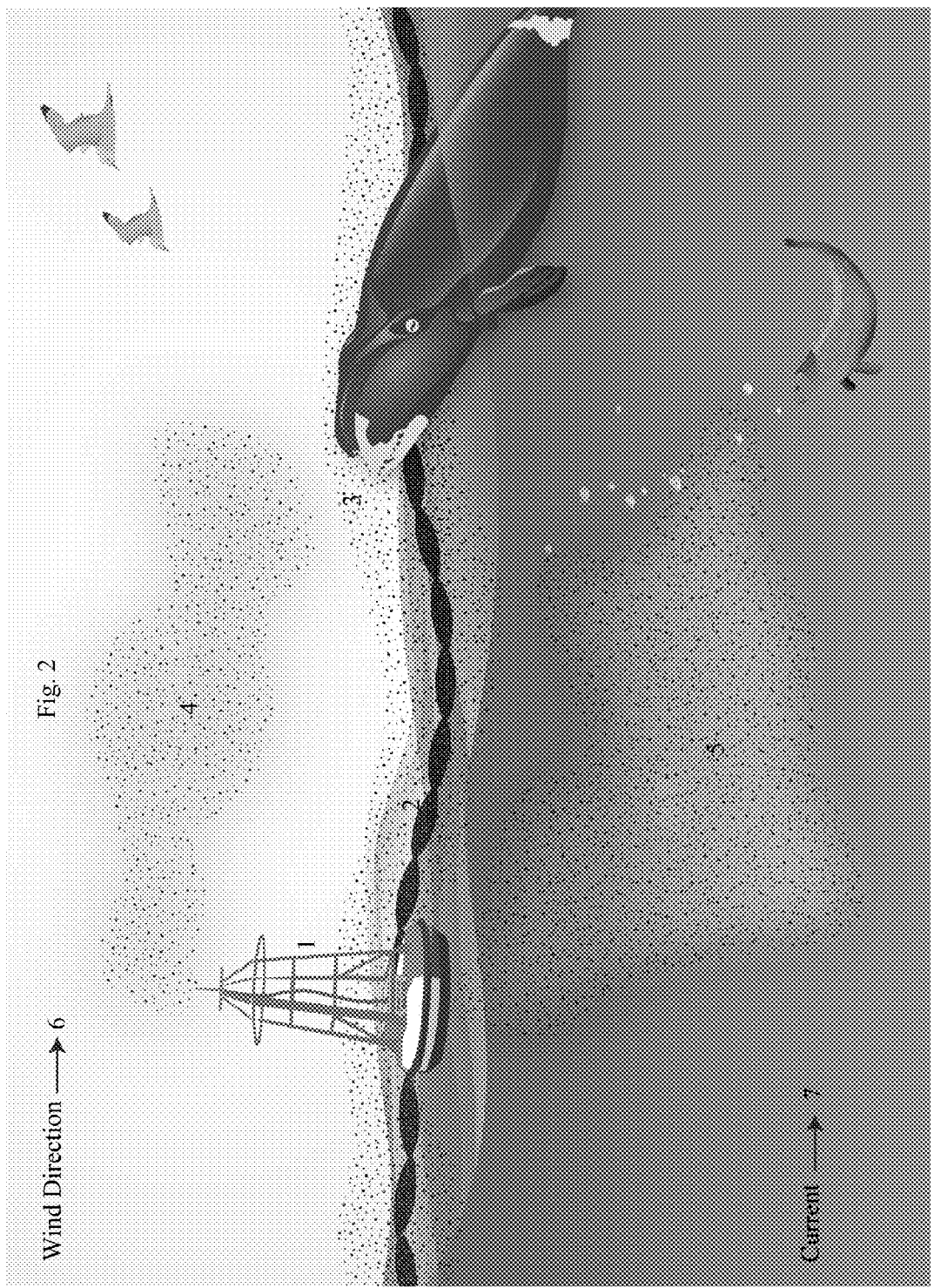

METHOD OF USING BIOLOGICALLY-RELEVANT CHEMICAL ATTRACTANTS FOR MARINE PREDATORS

CROSS-REFERENCE TO RELATED APPLICATIONS

This application claims the benefit of U.S. Provisional Application No. 61/816,656 filed on 26 Apr. 2013 which is incorporated in its entirety by this reference.

STATEMENT REGARDING FEDERALLY SPONSORED RESEARCH OR DEVELOPMENT

This invention has not, as of the time of filing, been the subject of any federally sponsored research or development.

STATEMENT REGARDING PRIOR DISCLOSURES BY AN INVENTOR OR JOINT INVENTOR

This invention was the subject of a presentation to the public by inventor on 27 Apr. 2012 entitled "Baleen whales and tubenose seabirds—a colossal chemosensory convergence?" At the 34th Meeting of the Association for Chemoreception Sciences, Huntington Beach, Calif.

FIELD OF THE INVENTION

This invention relates to a new method for artificially attracting marine predators, specifically a new method to enable the method user to entice and predictably move marine predators in a desired direction by deploying gradients of marine indicator attractants, such as those reliably associated in nature with food sources.

BACKGROUND OF THE INVENTION

Though it is widely believed that all whales cannot smell, evidence points to the contrary, including indigenous knowledge, anatomical, genetic and behavioral data. Many whales face a feeding "problem" that is similar to tubenose seabirds (e.g. petrels, shearwaters). Classic seabird studies reveal that tubenoses use olfactory-mediated foraging by orienting into the wind upon approaching experimental "plumes" of food scent. More recent work has discovered some marine birds are attracted to dimethyl sulfide (DMS), a volatile chemical byproduct of algae (phytoplankton) when it is being fed upon by zooplankton. Hence, for a marine predator like a seabird, DMS is a potentially reliable chemical indicator of a zooplankton food source and a rich place to feed.

Until recently, any behavioral evidence indicative of a whale's ability to smell was completely lacking. The inventor's recent field research on Humpback whales (*Megaptera novaeangliae*) in southeast Alaska revealed that whales orient into the wind significantly more often than expected by chance alone (n=231 whales, df=1, $X^2$=54.6, P<0.0001). This pattern is consistent with a capacity detect chemical stimuli carried by wind. Other baleen whale species (Suborder Mysticeti), like humpbacks, may also detect air- or water-borne chemical stimuli, as they have measurable olfactory structures and large trigeminal nerves, which may also perceive chemical irritation. Toothed whales, however, such as dolphins or Sperm whales (Suborder Odonticeti) appear to lack olfactory anatomy, but may still sense chemical irritation.

When whales or other marine predators feed, they are likely exposed to a number of biologically-relevant chemical stimuli in both air and seawater that are associated with a productive food patch. For example, zooplankton grazing on algae rip open algal cells and release the algal metabolite DMSP (dimethyl sulfoniopropionate) into seawater. DMSP rapidly breaks down into DMS (dimethyl sulfide) and acrylic acid, or it may follow another degradation pathway to produce methanethiol. Hence, the chemicals are indirectly indicative of food, as they are not directly derived from zooplankton prey itself, but rather derived from the plant food (algae) that zooplankton are actively consuming. Different marine habitats exhibit different concentrations of the aforementioned chemicals. Concentrations are positively associated with areas of high productivity, but they can vary by season and geographic location. For example, DMS concentrations in highly productive "hot spots" of Arctic Oceans can reach 4.0-7.0 nM, whereas underneath marine ice they may be only 0.4-2.0 nM.

Synthetic and/or natural sources or mixtures of biologically-relevant attractants (e.g. DMS, DMSP, acrylic acid and/or methanethiol) could provide a very new and powerful method to attract baleen whales. The luring mechanism mimics a high-quality feeding site, and thereby attracts baleen whales in a predictable direction, up a chemical gradient, toward an artificial stimulus source. An alternate embodiment of this idea includes not only whales, but a variety of other marine vertebrate predators (e.g. sea turtles, basking sharks, seals, sea lions, birds, fish), which have been positively correlated with DMS in their environment, or shown to perceive DMS in a laboratory setting.

The aforementioned attractant or luring mechanism would fundamentally alter how humans manage the difficult task of motivating large marine creatures like whales to move in a desired direction, for instance away from a dangerous oil spill or other marine hazard. State of the art knowledge focuses on loud, acoustic deterrents, including cannon guns, pounding on hollow steel pipes (called Oikami pipes), low flying aircraft, harassment by vessels, or underwater "pingers" attached to hazardous equipment. Collectively, the state of the art "hazing" methods have a number of disadvantages. First, loud noises that aim to scare animals produce highly variable reactions, making behavioral responses erratic, unpredictable, and can include the undesirable result of an animal moving closer to a hazard. Second, even acoustic devices, such as pingers, that whales can hear but are not loud enough to cause cause hearing damage (e.g. 135 dB), have a limited underwater range (<100 m). Thus, desirable improvements of a biologically-relevant lure, include predictable, directed movement or attraction toward an attractant source, as well as a long distance range for stimulus perception. Chemical stimuli can provide both such improvements.

Management agencies in charge of marine hazards, such as oil spills, emphasize the need to have multiple tools for wildlife relocation ready to deploy during a marine emergency. Attractants are needed, but there are few, if any, relative to the variety of hazing techniques currently available. Unlike hazing, attractants are amendable to gradually and/or reliably enticing animals to move in a preferred direction.

A powerful means of attracting animals engages multiple animal senses at once. A biologically-relevant attractant has the potential to stimulate the three vertebrate chemical senses: smell, taste, and the trigeminal system. Trigeminal responses in humans, for example, include the mild irritation or tickle of mucous membranes when exposed to chemicals, such as those in ground pepper. In some whales such as the baleen whale, the trigeminal nerve is the largest cranial nerve. The compound DMS exhibits properties that produce both marked olfactory and trigeminal responses. An alternate embodiment of the lure could enhance multimodality and the attractive value of the stimulus by combining a chemical attractant with one or more cues that are perceived by entirely different sensory modalities. For example, along with chemical stimuli, one might provide an auditory stimulus, such as underwater playback of whale song.

SUMMARY OF THE INVENTION

Disclosed herein is a method of using, as separate signals or in combination, dimethyl sulfide (DMS), dimethyl sulfoniopropionate (DMSP), acrylic acid and/or methanethiol or other biologically-relevant attractants for marine top predators, including mammals (whales, seals, sea lions), sea turtles, fish and birds. The method described herein involves introducing attractants into the air and seawater, via a single or an array of deployment devices, in order to attract and move animals in a desired direction, along one or more gradient(s) or chemical plume(s). Deployment can be optimized by assessing wind and water current velocity and direction, as well as deploying a single device or an array of devices (on land, sea, or air) and thereby facilitating or fine-tuning animal movement in a single or multiple desired direction(s).

The method of using this attractant allows the method user to facilitate the movement of marine predator species in a predictable manner, including animals that are extremely large, rare or endangered. Present methods for moving whales, for example, rely on aversive stimuli (loud noises), whereas the invention focuses on an attractive stimulus or stimuli that mimics or magnifies the odor characteristics of a high-quality food source, or other behavioral situation, to which animals are naturally motivated to seek.

The goal of the invention is to relocate individual animals or animal groups. Relocation may be necessary due to a hazardous or harmful situation, including, but not limited to, oil spills and other clean-up activities, off-shore drilling, and/or shipping lanes. Additional advantages of the invention will be set forth in part in the description which follows or may be learned by practice of the invention. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate an embodiment of the invention, and together with the description, serve to explain the principles of the invention.

FIG. 1 and FIG. 2 illustrate different methods of using an attractant for marine predators, such as marine mammals (whale and seal depicted), birds (depicted) or other predators (not depicted, such as fish, sea turtles).

FIG. 1 specifically depicts a simplified situation in which a single buoy device 1 introduces an attractant as gradients or "plumes" into the air 2 (wind direction indicated 3) and water 4 (current direction indicated 5). Animals are attracted to and move up the gradient in the desired direction (toward the buoy, or scent source).

FIG. 2 depicts a more complicated situation that includes not only a buoy 1, but also a "boom-like" device 2, similar to what is used in an oil spill clean up. The difference is that the boom is soaked in the attractant, and thereby creates a continuous "line" of attractant 3, which can serve as another means of directing animal movements, in addition to the "plumes" in air 4 and in water 5. FIG. 2 demonstrates the degree of flexibility with regard to deployment, which depending on the location of the marine hazard, wind direction 6 and current direction 7, may involve one or more deployment mechanisms, devices or arrays.

DETAILED DESCRIPTION OF THE INVENTION

Figure 1:
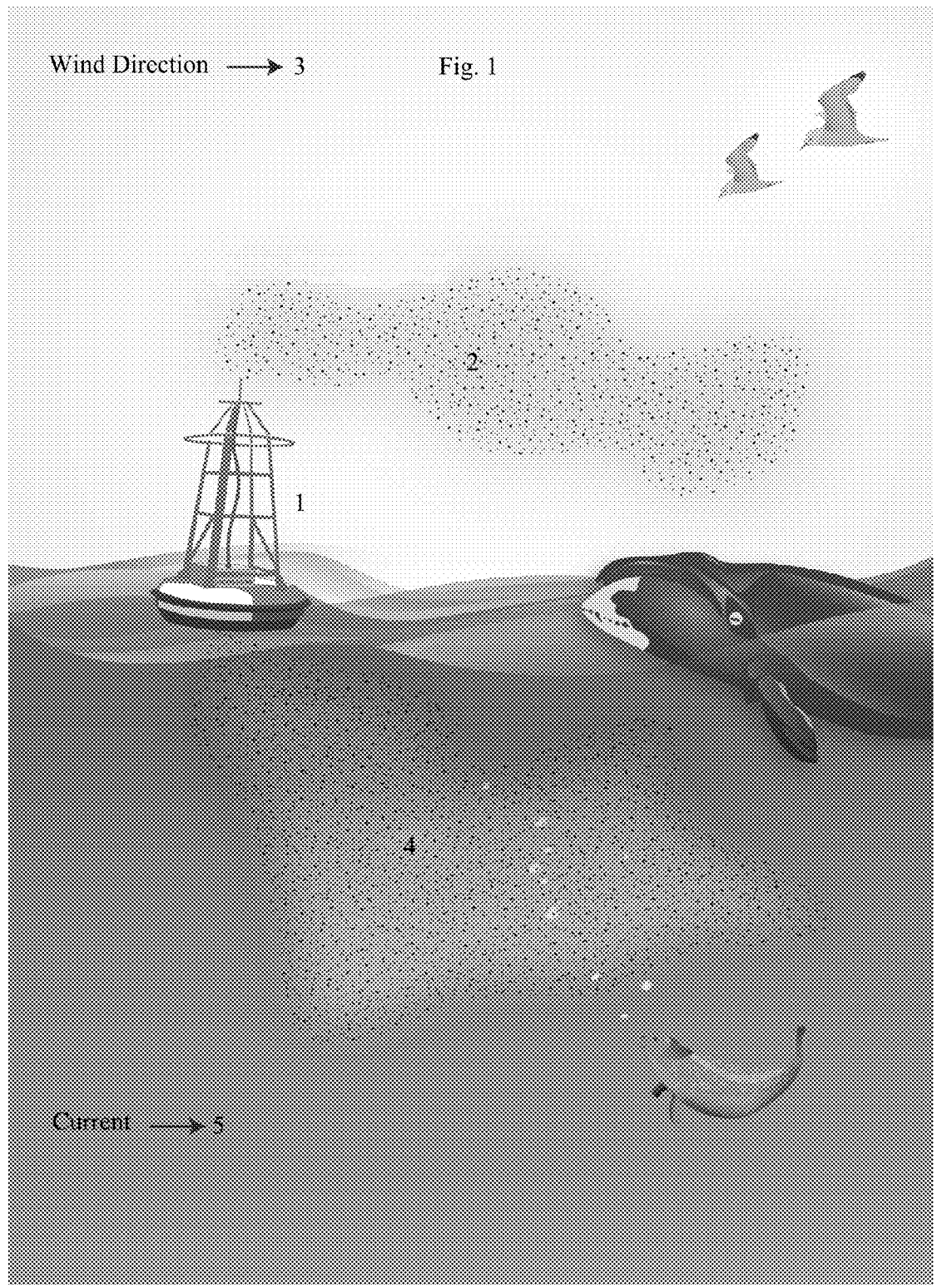

Before the present method is disclosed and described, it is to be understood that this invention is not limited to specific methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

The present invention may be understood more readily by reference to the following detailed description of the preferred embodiment of the invention and the examples included therein and to the Figures and its previous and following description.

Disclosed herein is a method of using biologically-relevant attractants, such as dimethyl sulfide (DMS), dimethyl sulfoniopropionate (DMSP), acrylic acid and/or methanethiol to attract top marine predators, including mammals (whales, seals, sea lions), sea turtles, basking sharks, fish and birds. The method described herein involves artificially deploying attractants into the air and water at the location to which the method user seeks to attract marine predators. Deployment effectively disperses the biologically-relevant stimulus over a large area of open air and/or water.

Artificially deploying the attractants into air and seawater provides a biologically relevant mechanism to entice marine predators along a single or series of chemical gradients, which mimic the proximity of a high-quality feeding site. Such attractants have the advantage of allowing the method user to predictably affect the movement of marine predators. Deployment can be optimized by assessing wind and water current velocity and direction, as well as deploying a single device, or, optionally an array of devices (on land, sea, and/or air) thereby creating one or more attractant gradients that facilitate and fine-tune animal movement in a single or multiple desired direction(s).

This invention enables the method user to relocate marine predators away from a hazardous situation, including, but not limited to, oil spills and clean-up activities, off-shore drilling, and shipping lanes. Such attractants are also useful to entities wishing to lure marine predators in a specific direction, for example, away from danger created as a result of the activities being performed by the method user in locations in which marine mammals generally pass through or congregate.

Deployment of biologically-relevant attractants may be completed through dispersal of volatiles into the air (e.g. via misting, spritzing, spraying, atomization, evaporation or other suitable process), coupled with depositing, injecting or broadcasting DMS or other attractants directly into the water column at appropriate depths to attract the marine predators. Wind movement can create a plume of odor, whereas currents create a waterborne plume at an appropriate depth. Predators then locomote up the concentration gradient of the chemical plume(s).

Movements can be fine-tuned through an assessment of wind and water direction and velocity relative to the hazard that the method user wishes the animals to avoid. Such parameters can inform the number, type and array or configuration of attractant-emitting devices that will optimally influence animal movements. Different plumes can be created by the single or an array of deployment source(s), or, optionally, a single continuous "line" that emits the stimulus, such as a floating boom. Combined, deployment effectively disperses attractants in a manner that mimics an ecologically relevant, alluring source location, such as an attractive food-related stimulus. The stimulus may be deployed as single or multiple gradients over a large area of open air and/or water.

Stimuli can be introduced into air or water via a number of methods, including but not limited to buoy system(s), the use of floating booms soaked in attractant, or other remote deployment techniques, such as unmanned aerial vehicles, an aerial glider system, or underwater vehicle. Deployment could also be done manually on-site (e.g. from shipboard, along the ice edge, or from land) by the method user(s). The air and water deployment coupled by device arrays provide an opportunity to create one or more attractant plumes or gradients along which marine predators will be motivated to move. Furthermore, detection in air and water enhances the efficacy of the method by stimulating multiple chemical senses, including smell, taste, and the trigeminal system. Targeting multiple sensory systems of a marine animal increases the likelihood the DMS stimulus will be detected, and enhances the magnitude of attraction toward the deployment site.

What is claimed is:

1. A method for controlling the movement of marine predators, which comprises:

(a) releasing an effective amount of an attractant composition into a marine environment such that the marine predators are motivated to move towards said attractant composition;

(b) wherein said attractant composition is selected from the group consisting of dimethyl sulfide, dimethylsulfoniopropironate, acrylic acid and methanethiol.

2. The method of claim 1, wherein said attractant composition is dimethyl sulfide.

3. The method of claim 1, wherein said marine predators are whales.

4. A method for attracting marine predators comprised of releasing an attractant composition into the water of a marine environment, wherein said composition is selected from the group consisting of dimethyl sulfide, dimethylsulfoniopropionate, acrylic acid and methanethiol.

5. The method of claim 4, wherein said composition is released into the water of a marine environment from at least one point source device containing an effective amount of the attractant composition.

6. The method of claim 5, wherein said composition is additionally released from a linear device containing an effective amount of the attractant composition.

7. The method of claim 4, wherein said composition is released into the water of a marine environment from at least one linear device containing an effective amount of the attractant composition.

8. The method of claim 4, wherein said composition is released manually into the water from at least one location on a ship inside said marine environment, from the shoreline or ice edge near said marine environment.

9. The method of claim 4, wherein said attractant composition is used in combination with an attractive auditory or other sensory cue relevant to the marine predators.

10. The method of claim 4, wherein said composition is additionally released into the air of a marine environment by misting, spritzing, spraying, volatilization, evaporation, or atomization.

11. The method of claim 10, wherein release of said composition is optimized relative to wind and/or water direction and velocity.

12. The method of claim 10, wherein said composition may be aerially dispersed using remote deployment vehicles, aircraft, or underwater vehicles.

13. The method of claim 10, wherein said attractant composition is used in combination with an auditory or other sensory attractant.

14. A method for attracting marine predators by releasing an attractant composition into the air of a marine environment, wherein said composition is selected from the group consisting of dimethyl sulfide, dimethylsulfoniopropionate, acrylic acid and methanethiol.

15. The method of claim 14, wherein said composition is released into the air of a marine environment by misting, spritzing, spraying, atomization, or evaporation or equivalent releasing devices.

16. The method of claim 14, wherein said composition may be aerially dispersed using remote deployment vehicles, aircraft, or underwater vehicles.

17. The method of claim 14, wherein release of said composition is optimized relative to wind and current direction and/or velocity.

18. The method of claim 14, wherein said attractant composition is used in combination with at least one auditory or other sensory attractant.

* * * * *